United States Patent [19]

O'Farrell et al.

[11] Patent Number: 4,973,844
[45] Date of Patent: Nov. 27, 1990

[54] VEHICULAR MOISTURE SENSOR AND MOUNTING APPARATUS THEREFOR

[75] Inventors: Desmond J. O'Farrell, Holland; Kenneth L. Schierbeek, Zeeland, both of Mich.

[73] Assignee: Donnelly Corporation, Mich.

[21] Appl. No.: 377,942

[22] Filed: Jul. 10, 1989

[51] Int. Cl.[5] ............................................ G01N 21/41
[52] U.S. Cl. .................................. 250/341; 15/250 C; 250/339; 250/349
[58] Field of Search ...................... 250/339, 341, 349; 318/444, 480, 483, DIG. 2; 15/250 C; 340/602

[56] References Cited

U.S. PATENT DOCUMENTS

| | | | |
|---|---|---|---|
| 3,307,095 | 2/1967 | Redmond, Jr. | 318/483 |
| 3,555,289 | 1/1971 | Sobkow | 307/10.1 |
| 3,619,614 | 11/1971 | Yamaka | 250/352 |
| 3,649,898 | 3/1972 | Inoue | 318/483 |
| 3,660,659 | 5/1972 | Eisenman et al. | 250/352 |
| 3,689,814 | 9/1972 | Holt | 318/266 |
| 3,743,056 | 7/1973 | Zitelli et al. | 187/134 |
| 3,786,330 | 1/1974 | Inoue et al. | 318/483 |
| 3,794,847 | 2/1974 | Cadiou | 15/250 C |
| 3,826,979 | 7/1974 | Steinmann | 324/61 R |
| 3,925,244 | 12/1975 | Nagasawa et al. | 250/372 |
| 3,977,792 | 8/1976 | Jumonji et al. | 356/445 |
| 4,010,383 | 3/1977 | Grassmann | 307/118 |
| 4,131,834 | 12/1978 | Blaszkowski | 318/483 |
| 4,139,801 | 2/1979 | Linares | 315/83 |
| 4,229,653 | 10/1980 | Uthe | 250/339 |
| 4,317,073 | 2/1982 | Blaszkowski | 318/483 |

(List continued on next page.)

FOREIGN PATENT DOCUMENTS

| | | |
|---|---|---|
| 0175362 | 3/1986 | European Pat. Off. . |
| 2101319 | 7/1972 | Fed. Rep. of Germany . |
| 2741653 | 3/1979 | Fed. Rep. of Germany . |
| 3206029 | 4/1983 | Fed. Rep. of Germany . |
| 3244767 | 6/1984 | Fed. Rep. of Germany . |
| 54-110529 | 8/1979 | Japan . |
| 57-22945 | 2/1982 | Japan ........................ 15/250 C |

(List continued on next page.)

OTHER PUBLICATIONS

U.S. patent application Ser. No. 07/298,419, by Hochstein, filed Jan. 18, 1989, entitled "Rain Sensor with Reference Channel".

Co-pending U.S. patent application Ser. No. 07/183,706, filed Apr. 19, 1988, entitled "Vehicular Moisture Sensor and Mounting Apparatus Therefor", assigned to the same assignee as the present invention. The apparatus of this application was provided in three prototype samples for technical evaluation and testing (List continued on next page.)

*Primary Examiner*—Constantine Hannaher
*Attorney, Agent, or Firm*—Price, Heneveld, Cooper, DeWitt & Litton

[57] ABSTRACT

A moisture sensing assembly, adapted for mounting on the inner surface of a vehicle window or windshield to control vehicle accessories such as windshield wipers, maximizes the window are a being sensed while minimizing the size of the overall assembly. In the preferred embodiment, moisture on the outer window surface is detected by stacked rows of infrared energy receiving sensors spaced in angular relationship from stacked rows of infrared energy emitting diodes. The emitter diodes and sensors are preferably carried in separate emitter and detector mounting blocks slidably fitted in a rigid carrier. The sensor row closest to the window receives energy from the diode emitter row farthest from the window and vice versa. Energy barrier walls are provided in the diode and sensor support for blocking energy reflected by the inside window surface. The assembly is adapted for use with an electrical circuit which operates one emitter diode row and its corresponding sensor row while the other emitter and sensor rows are deactivated to prevent interference and false reflected signals from the other emitter row. Removable attachment to the window with a circular member provides ease of installation and improved positioning and orientation of the sensing assembly.

53 Claims, 6 Drawing Sheets

U.S. PATENT DOCUMENTS

| | | | |
|---|---|---|---|
| 4,339,698 | 7/1982 | Kearns | 318/444 |
| 4,355,271 | 10/1982 | Noack | 318/480 |
| 4,394,605 | 7/1983 | Terazawa | 315/280 |
| 4,463,294 | 7/1984 | Gibson | 388/812 |
| 4,476,419 | 10/1984 | Fukatsu et al. | 318/444 |
| 4,481,450 | 11/1984 | Watanabe et al. | 318/444 |
| 4,495,452 | 1/1985 | Boegh-Peterson | 318/444 |
| 4,542,325 | 9/1985 | Kobayashi et al. | 318/483 |
| 4,554,493 | 11/1985 | Armstrong | 318/444 |
| 4,588,935 | 5/1986 | Kaneiwa et al. | 318/483 |
| 4,589,771 | 5/1986 | Watanabe et al. | 356/38 |
| 4,595,866 | 6/1986 | Fukatsu et al. | 318/444 |
| 4,620,141 | 10/1986 | McCumber et al. | 318/483 |
| 4,636,643 | 1/1987 | Nakamura et al. | 250/338.1 |
| 4,636,698 | 1/1987 | Leclercq | 318/443 |
| 4,652,745 | 3/1987 | Zanardelli | 250/227 |
| 4,676,638 | 6/1987 | Yasuda | 356/237 |
| 4,689,536 | 8/1987 | Iyoda | 318/483 |
| 4,701,613 | 10/1987 | Watanabe et al. | 250/227 |
| 4,798,956 | 1/1989 | Hochstein | 250/341 |
| 4,859,867 | 8/1989 | Larson et al. | 307/10.1 |
| 4,871,917 | 10/1989 | O'Farrell et al. | 250/341 |

FOREIGN PATENT DOCUMENTS

| | | | |
|---|---|---|---|
| 58-118436 | 7/1983 | Japan . | |
| 58-185339 | 10/1983 | Japan . | |
| 58-199253 | 11/1983 | Japan . | |
| 59-14563 | 1/1984 | Japan | 15/250 C |
| 59-84141 | 5/1984 | Japan . | |
| 59-85944 | 5/1984 | Japan | 340/602 |
| 59-89250 | 5/1984 | Japan | 15/250 C |
| 59-100034 | 6/1984 | Japan . | |
| 59-106348 | 6/1984 | Japan | 15/250 C |
| 60-78844 | 5/1985 | Japan . | |
| 60-174348 | 9/1985 | Japan . | |
| 60-174931 | 9/1985 | Japan . | |
| 60-179648 | 9/1985 | Japan . | |
| 60-216245 | 10/1985 | Japan | 340/602 |
| 60-216246 | 10/1985 | Japan | 340/602 |
| 61-116645 | 6/1986 | Japan | 340/602 |
| 1101441 | 1/1968 | United Kingdom . | |
| 1150384 | 4/1969 | United Kingdom . | |
| 1321221 | 6/1973 | United Kingdom . | |
| 1382261 | 1/1975 | United Kingdom . | |

OTHER PUBLICATIONS in an automotive environment and not for purposes of sale to one other company more than one year prior to Jul. 10, 1989.

Co-Pending U.S. patent application Ser. No. 07/183,693, filed Apr. 19, 1988, entitled "Windshield Moisture Sensing Control Circuit", assigned to the same assignee as the present invention.

Co-Pending U.S. patent application Ser. No. 07/317,288, filed Feb. 28, 1989, entitled "Continuously Adaptive Moisture Sensing System for Wiper Control", assigned to the same assignee as the present invention.

Co-Pending U.S. patent application filed Jul. 10, 1989, entitled "Control for a Moisture Sensor", assigned to the same assignee as the present invention.

Quantex Engineering, Warren, Mich.—"Bench Test With Solar World Cells for Compensated Rain Sensor" (two pages).

"E. O. Rain Sensor—Compensation Methods" (one page).

Siemen Opto-Electronic Data Book—1986, pp. 532–534 and 538 (LD271-Application Notes) (four pages).

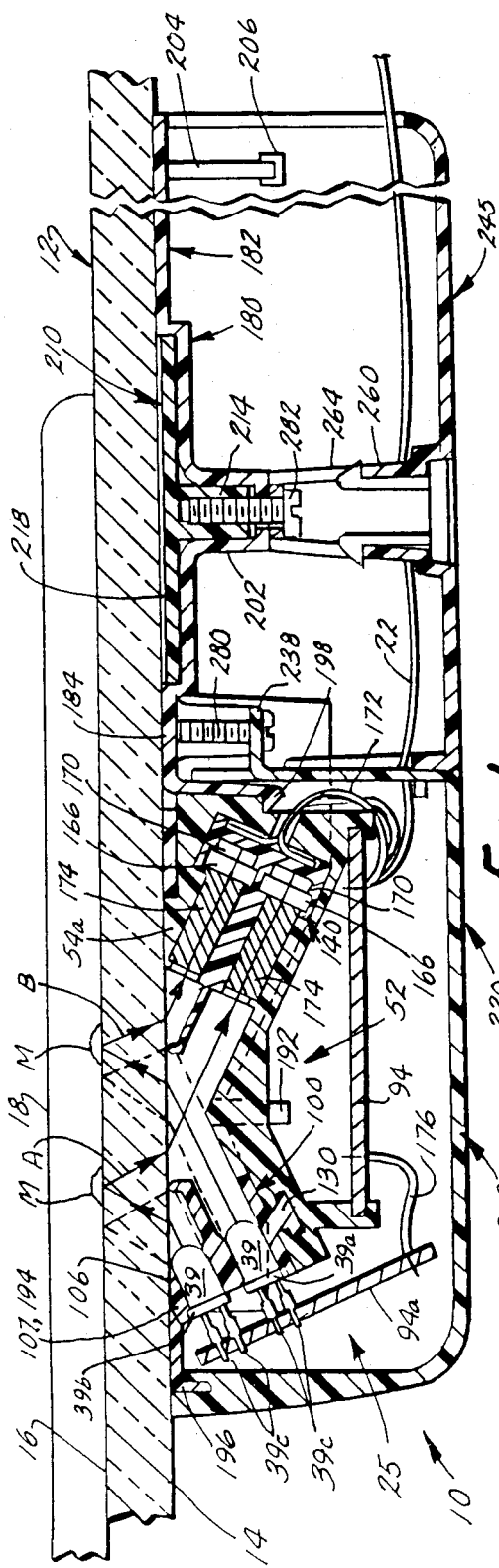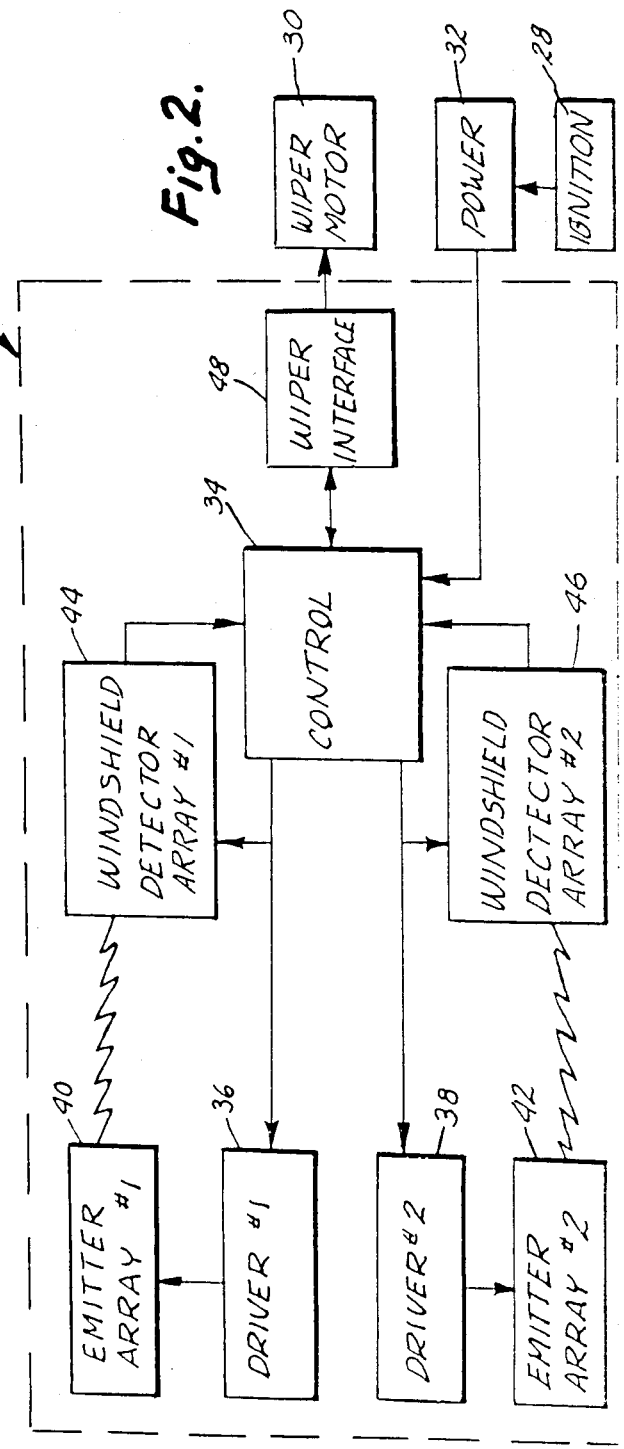

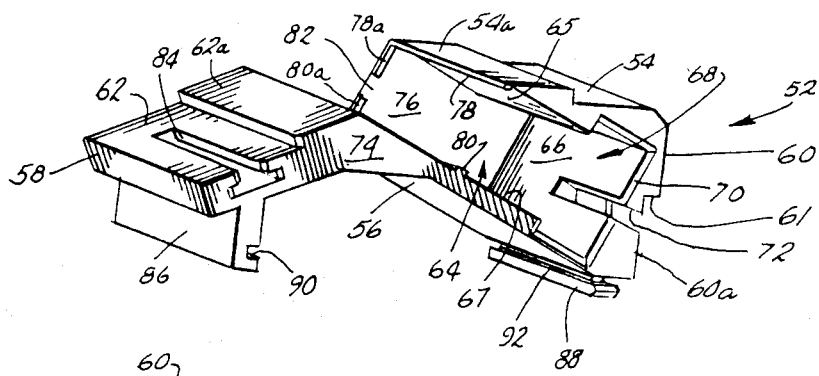
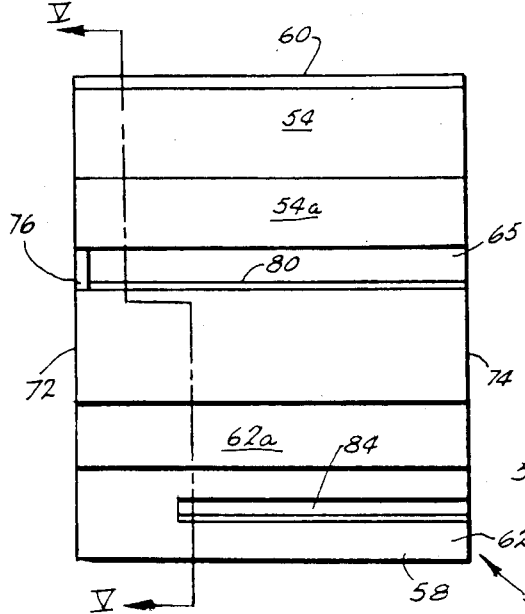
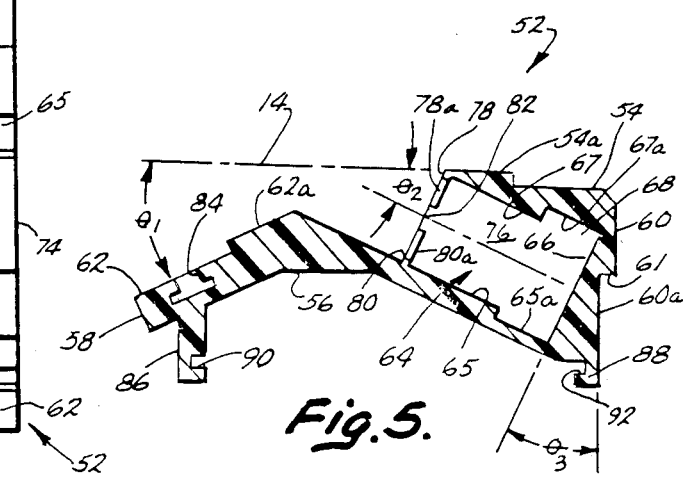
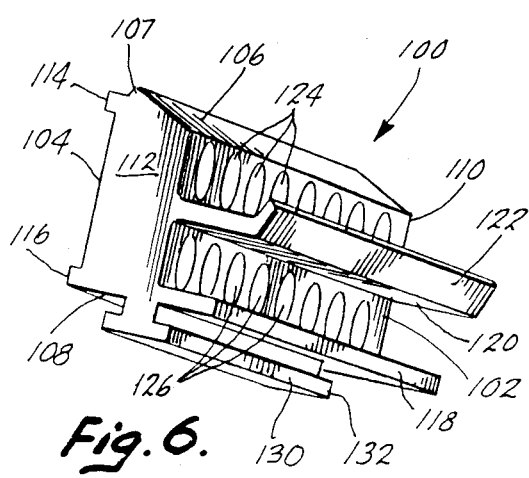
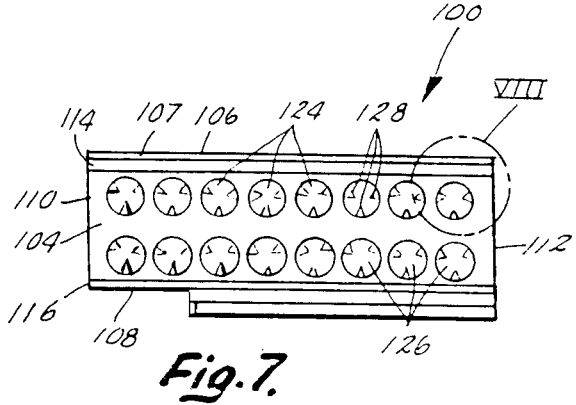

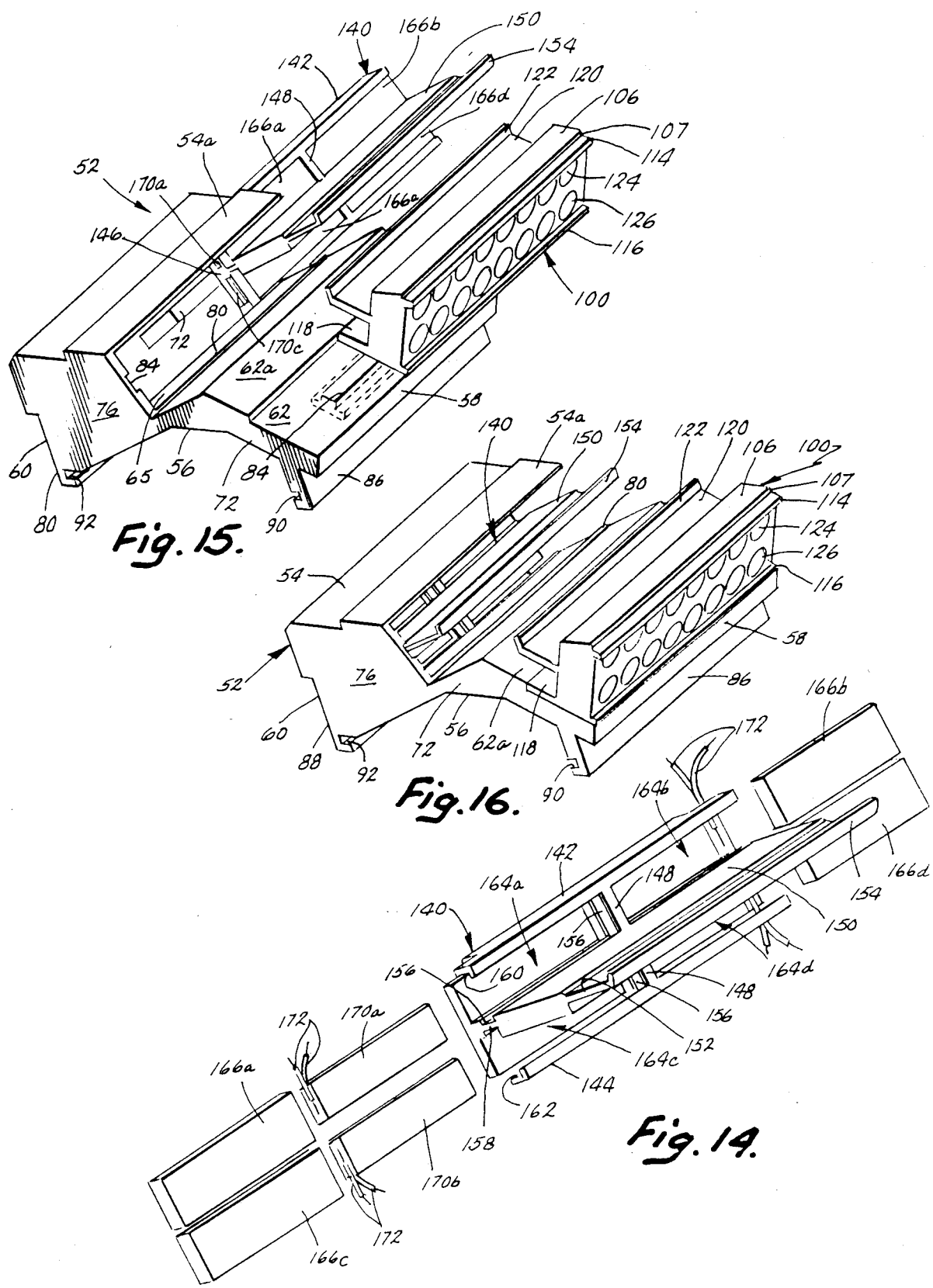

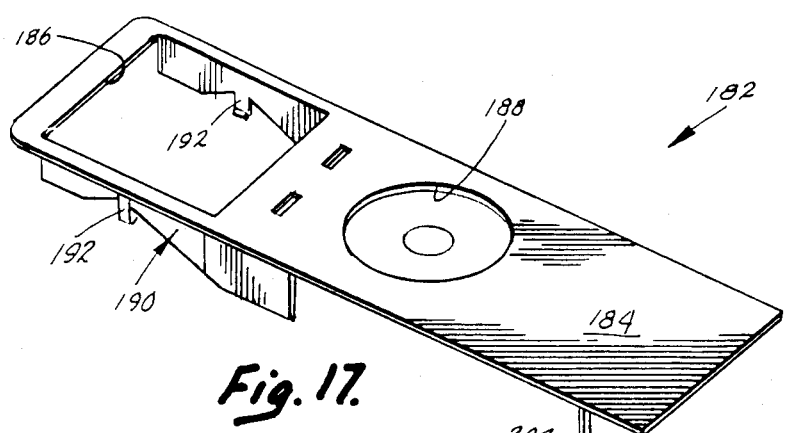
Fig. 17.
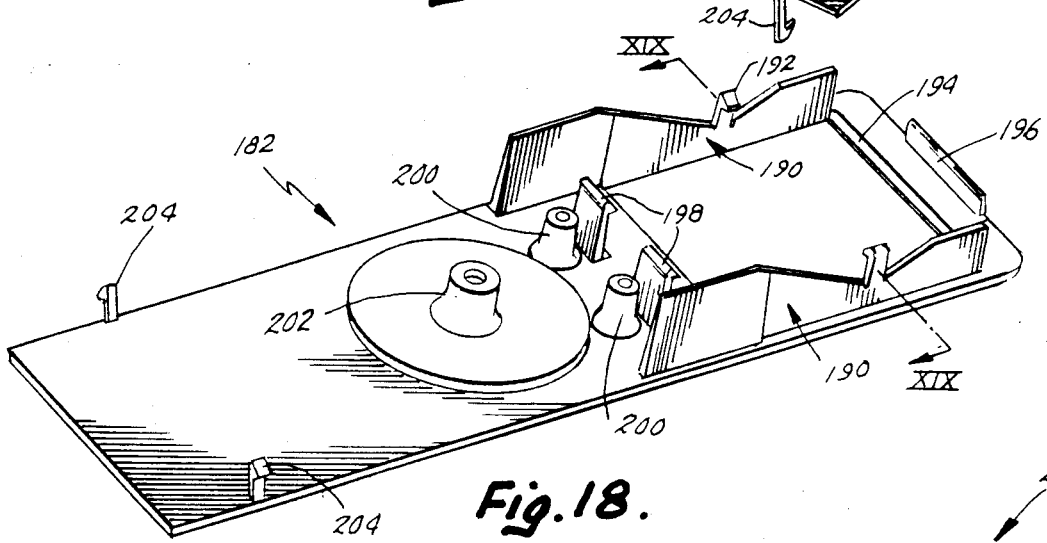
Fig. 18.
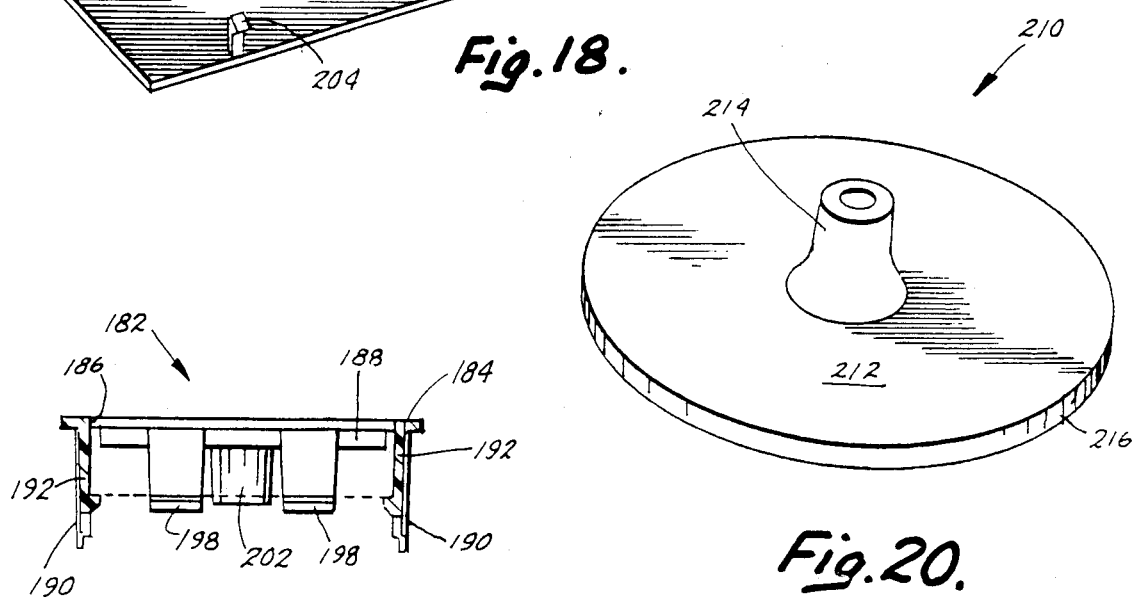
Fig. 19.
Fig. 20.

VEHICULAR MOISTURE SENSOR AND MOUNTING APPARATUS THEREFOR

BACKGROUND OF THE INVENTION

This invention relates to moisture sensors for detecting moisture such as rainfall and dew as well as other matter such as dirt, dust, salt film and the like on windows. The invention is especially adapted for vehicle windows to control accessories such as windshield wipers and the like. More particularly, the invention concerns an optical sensing apparatus and assembly for mounting on one side of a window panel for detecting moisture and other matter on the opposite side of the window panel while maximizing the area sensed and minimizing the overall assembly size.

Various types of moisture sensing apparatus have been used on vehicles to control accessories such as windshield wipers. Optical moisture sensors have been found particularly useful since they require no special coatings or other structure on the exterior of the window or vehicle for physically contacting rainfall or moisture. One such device employs an infrared emitter and detector which senses infrared energy emitted from inside the windshield or window and refracted and reflected back at decreased levels when moisture or other matter is present on the outside of the windshield to a detector also mounted on the interior of the vehicle. Such a sensor is disclosed in U.S. Pat. No. 4,798,956 and includes an emitter which emits pulses of infrared energy toward the inside surface of a window at an incident angle. The radiant energy is refracted into the window at the inside air/window surface and reflected off the air/outside window surface back through the window where it is again refracted and detected by a detector/sensor positioned along a reflection angle equal to the incident angle. The emitter and detector are spaced and positioned at predetermined locations and angles all as set forth in U.S. Pat. No. 4,798,956.

As an improvement over the moisture sensing device of U.S. Pat. No. 4,798,956, an optical moisture sensing device which compensates various environmental conditions is disclosed in co-pending, commonly assigned U.S. Pat. No. 4,871,927. That improved device provides stable operation over a range of operational temperatures, over the lifetime of the unit, and in varying types of environmental and ambient light conditions. Moreover, a mounting apparatus is provided which secures the device in proper geometrical relationship adjacent a window surface and provides a protective enclosure for the sensing device and associated wiring. The mount is detachably fastened to the window for removal and replacement when repairs or window replacement are necessary.

Use of the above sensing devices revealed that the area of the window being sensed was relatively small, and that the probability of moisture impinging on the sensed area was likewise small, especially in light rain conditions. Thus, in conditions where a relatively small and scattered number of raindrops strike the vehicle and its window areas, the probability of such a drop falling on the sensed area and being indicated to control the desired vehicle accessory (such as the windshield wipers) often prevented operation of the wipers until long after significant rain had begun to fall.

The prior sensing devices were also relatively difficult and tedious to assemble and were relatively difficult to properly test prior to final assembly. Further, the mounting assembly for securing the sensing device to the windshield required precise, accurate positioning on the inside windshield/window surface in order to orient the sensing unit properly when mounted. This required extra care and time during installation on vehicles thereby increasing costs for use of the device.

Therefore, a need was recognized for an improved moisture sensing device of the optical type which would maximize the window area being sensed while minimizing the size of the sensing assembly. It was also desired to provide reduced complexity and difficulty in manufacturing the sensing device while providing opportunities for testing various components of the overall assembly prior to incorporation in the final unit. Further, it was desired to provide an improved mounting structure which could be more quickly installed while allowing easier orientation of the sensing device in its operational position.

SUMMARY OF THE INVENTION

Accordingly, the present invention provides an improved moisture sensing device based on the optical sensing principles disclosed in U.S. Pat. No. 4,798,956. A plurality of energy emitting diodes and energy receiving photosensors are preferably arranged in a stacked relationship which maximizes the area sensed for moisture and other matter while minimizing the size of the overall sensing assembly. The invention also provides improved ease of assembly and allows testing of individual component subassemblies prior to final assembly. In addition, an improved mounting system is included which allows faster and simpler installation of the moisture sensor on a windshield or window followed by rapid orientation and positioning without requiring tedious and precise alignment of the various mounting components during installation.

In one form, the invention is a moisture sensing assembly for mounting on one surface of a window to detect and indicate moisture or other matter accumulated on the opposite surface of the window. First and second emitter means emit radiant energy toward the window. First and second detector means detect and receive radiant energy from the first and second emitter means, respectively, after reflection and refraction by the window and any accumulated moisture or other matter on the opposite surface of the window. Radiant energy barrier means prevent reflection of radiant energy from the first emitter means and the one surface of the window to the first and second detector means and prevent reflection of radiant energy from the second emitter means and the one surface of the window to the second detector means. Support means provide support for the first and second emitter means in spaced angular relationship to the first and second detector means as well as the radiant energy barrier means on the one window surface.

Preferably, the radiant energy barrier means include first and second barrier walls spaced from one another and extending between the emitters and detectors which, in the preferred embodiments, are infrared energy emitting diodes and infrared energy sensing photovoltaic cells. The emitters are preferably mounted in apertures provided in pairs, one aperture in each pair being closer to the window engaging surface of the support means than the other aperture. Similarly, the detector means are mounted in pairs of apertures, one of the apertures being closer to the window engaging surface than the other aperture. The assembly is adapted for use with an electrical circuit which operates the first emitter and first detector means concurrently, while the second emitter means and second detector means also operate concurrently but only when the first emitter and first detector means are not operating.

In other aspects of the invention, the emitters and detectors are mounted in a rigid carrier body in emitter mounting means and detector mounting means, respectively, each of which is removably attached to a different portion of the carrier body. The emitter mounting means includes apertures for receiving the emitter diodes while the detector mounting means is a block having a pair of parallel photosensor apertures, one being closer to the window engaging surface than the other.

Yet another aspect of the invention provides a circular mounting member for attachment to the surface of a window and mounting means for engaging and releasably mounting the moisture sensing unit on the window including means engaging the circular mounting member for positioning the moisture sensing unit as desired around that member. Releasable fastening means are provided to hold the mounting member and mounting means together until released.

Preferably, the circular mounting member is a circular disk while the mounting means is a plate having an opening and a plurality of resilient retaining members for holding the moisture sensing unit adjacent and in registry with the opening, the plate being sufficiently resilient to urge the sensing unit toward the window. In addition, housing means for covering the moisture sensing means and the circular mounting member as well as for enclosing, covering and shielding any electrical wiring extending from the moisture sensing unit are releasably secured to the mounting plate.

The invention provides an increased sensing area while optimizing the assembly size through the inclusion of stacked banks or rows of emitters and detectors/sensors which are held in compact fashion by a carrier block. Energy barrier walls prevent undesired reflected energy from improperly triggering the separate sensors. The device is designed for use with electrical circuitry for enhancing the elimination of interference and false signals between the separate sensing and emitting areas while also compensating for temperature, ambient light and aging characteristics of the electrical components. The assembly also provides easier installation and removal for repair and replacement purposes, and improved orientation adjustment without requiring tedious, time-consuming alignment techniques. The carrier mounting block provides improved geometry and control of emitter and detector component positioning. Assembly of the device requires minimum component handling yet allows preassembly of various subcomponents and testing of such subcomponents in assembled form prior to incorporation in the final assembly. Thus, the invention minimizes waste, provides easier assembly and installation, and improves performance and moisture sensitivity.

These and other objects, advantages, purposes and features of the invention will become more apparent from a study of the following description taken in conjunction with the drawings.

BRIEF DESCRIPTION OF THE DRAWINGS

FIG. 1 is a sectional side elevation of the improved moisture sensing assembly and mounting apparatus of the present invention when secured to the inside surface of a conventional vehicle windshield behind the area cleared by the vehicle windshield wiper;

FIG. 2 is a schematic block diagram of the moisture sensing electrical control system and its connection to the vehicle electrical system and windshield wiper motor;

FIG. 3 is a perspective view of the carrier mounting block of the present invention;

FIG. 4 is a plan view of the carrier mounting block shown in FIG. 3;

FIG. 5 is a side sectional elevation of the carrier mounting block shown in FIGS. 3 and 4 and taken along line V—V of FIG. 4;

FIG. 6 is a perspective view of the emitter mounting block prior to attachment to the carrier mounting block;

FIG. 7 is a rear elevation of the emitter mounting block shown in FIG. 6;

FIG. 14 is a perspective view of the detector mounting block with the photovoltaic sensor cells and infrared filter elements shown in exploded position;

FIG. 15 is a perspective view of the carrier mounting block of the present invention with the emitter mounting block and detector mounting block partially assembled thereto;

FIG. 16 is a perspective view of the fully assembled carrier mounting block with emitter and detector blocks positioned thereon;

FIG. 17 is a perspective view of the mounting plate of the present invention taken from the top side thereof;

FIG. 18 is a perspective view of the mounting plate shown in FIG. 17 taken from the bottom thereof;

FIG. 19 is a sectional end elevation of the mounting plate taken along plane XIX—XIX of FIG. 18;

FIG. 20 is a perspective view of the windshield mounting disk of the present invention;

DESCRIPTION OF THE PREFERRED EMBODIMENTS

Figure 8:
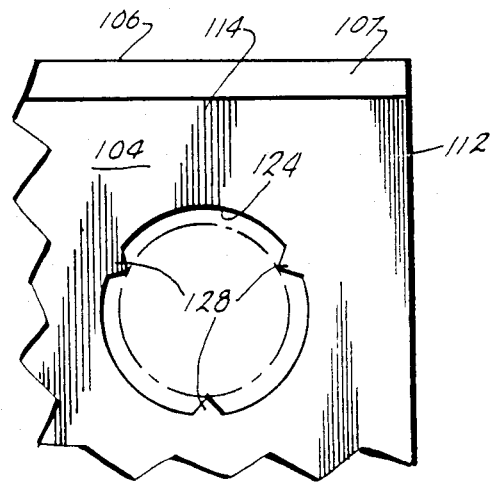
FIG. 8 is an enlarged elevation of one of the diode securing apertures of the emitter mounting block taken in area VIII of FIG. 7.

Referring now to the drawings in greater detail, a first embodiment 10 of the moisture sensing assembly for controlling vehicle accessories such as windshield wipers is illustrated in FIG. 1. Assembly 10 is adapted for mounting on the inside surface of a vehicle window 12 such as the front windshield for sensing the presence of moisture such as rainfall, dew and the like or other particles such as dust, dirt, salt residue or other matter on the exterior surface of the window. Preferably, window 12 is the front windshield of a vehicle with assembly 10 being mounted on inside surface 14 for sensing the presence of moisture and other matter on the exterior surface 16. Assembly 10 is preferably mounted adjacent a rearview mirror support (not shown) and may be used either with rearview mirrors secured directly to the inside windshield surface or with header mounted mirror structures. To function properly, it is necessary that the moisture sensing portion of assembly 10 be mounted within the sweep area of windshield wipers 18 which clear the exterior surface 16 of windshield 12.

As is also seen in FIG. 1, and as more fully explained below, sensing assembly 10 includes a housing assembly 220 which extends around the moisture sensing assembly and upwardly to the interior roof headliner of the vehicle (not shown). Any electrical wires 22 which extend from the moisture sensing unit of the assembly 10 are concealed by the elongated housing assembly 220 and the headliner as they extend into the vehicle wiring system. Such vehicle system may include a control switch for initiating operation of the moisture sensing assembly. The control switch assembly can be located in the vehicle headliner, or at other driver accessible locations such as on the turn signal stalk assembly, the instrument panel or other locations in the cockpit area.

As is also shown in FIG. 1, moisture sensing assembly 10 includes a moisture sensing unit 25 which is held and urged against the inside surface 14 of windshield 12 by a mounting structure 180 more fully described hereinafter. Sensing unit 25 includes a plurality of infrared energy emitting diodes 39 which emit and project infrared energy toward windshield glass 12 where, as explained below, the energy is refracted and reflected at the air-/exterior glass interface back through the glass and into infrared energy sensing photovoltaic cells 170 which convert the detected energy into an electrical current or signal. That signal is conveyed to an electronic control system on a circuit board 94 attached to the sensing unit. Board 94 is preferably a printed circuit board having circuit control elements printed thereon in conventional manner for controlling the operation of a windshield wiper system in response to the detected infrared energy.

In the preferred embodiments, sensing unit 25 is manufactured in accordance with the principles described in U.S. Pat. No. 4,798,956, issued Jan. 17, 1989, invented by Peter A. Hochstein entitled "ELECTRO-OPTICAL WINDSHIELD MOISTURE SENSING", the disclosure of which is hereby incorporated by reference herein. That application describes a moisture sensor and method for sensing moisture in which an infrared energy emitter emits pulses of infrared energy toward the inside surface of a windshield at a defined incident angle. The radiant energy is refracted into the window at the air/inside window surface and reflected off the air/outside window surface back through the window. The radiant energy is then detected by a photovoltaic detector at a reflection angle equal to the incident angle with respect to the glass surface. A support spaces the emitter and detector a distance D between the intersection of the axis of the emitter with the inside window surface and the intersection of the axis of the detector with the inside window surface which is determined by the following formula where T equals the thickness of the windshield glass, n is the index of refraction of the windshield glass and $\theta$ is the incident and reflection angle:

$$D = 2T \cos\theta (n^2 - \cos^2\theta)^{-\frac{1}{2}}$$

The present moisture sensing unit 25 is an improved version of the moisture sensor described in U.S. Pat. No. 4,798,956 which increases the size of the area sensed for moisture and other matter on the windshield while minimizing the overall size of the sensor assembly. Moisture sensing assembly 10 is also an improvement over the moisture sensing assembly shown in co-pending, commonly assigned U.S. Pat. No. 4,871,917, the disclosure of which is hereby incorporated by reference herein.

As shown in FIG. 2, the moisture sensing unit 25 of assembly 10 is powered through and controlled by an electronic circuit 26 connected to ignition 28 of the vehicle for control of a wiper motor or motors 30 in a windshield wiper system in the vehicle. When ignition 28 is switched on, DC power is supplied from a power circuit 32 to a control circuit 34 which, in turn, activates a pair of driver circuits 36, 38. Each driver circuit 36, 38, in turn, activates a plurality of infrared energy emitting diodes 39 contained in separate emitter diode rows or arrays 40, 42 (see also FIGS. 6 and 7). The diodes in arrays 40, 42 emit pulses of infrared energy which are detected after reflection and refraction at the windshield by separate detectors or photovoltaic sensor cells in rows or arrays 44, 46. Control 34 includes appropriate electrical circuitry such that driver 36 and emitter array or row 40 and detector row or array 44 are operated alternately from driver 38, emitter row or array 42 and detector row or array 46. One set of emitters and detectors is off while the other is on. Hence, stray, interfering infrared energy from one sensing set cannot be picked up by the other sensing set thereby avoiding false signals which could otherwise trigger the system. The control, therefore, energizes sensors 44 and 46 only when their corresponding diodes 40, 42, respectively, are pulsed on. When operating, the signals from detectors/sensors 44, 46 are fed to control circuit 34 which determines whether moisture is present on the exterior surface 16 of windshield 12 or whether high ambient infrared energy levels are present which should be ignored. In addition, control circuit 34 compensates for temperature variations affecting the output of emitters 40, 42 as well as any decreased infrared energy emission levels due to the age of the emitting diodes 40, 42 based on a reference signal which adapts to environmental conditions and other factors including temperature, ambient light and aging. Such reference signal is compared to the sensed signals and, when proper conditions have been met as determined by control circuit 34, wiper interface 48 and wiper motor 30 are activated to move wipers 18 across exterior surface 16 of the windshield 12 to clear moisture and other particles therefrom. Accordingly, when detectors 44, 46 and control circuit 34 indicate no moisture, operation of the wiper motor 30 is shut down through the wiper interface 48.

The details of the operation of control circuit 26 for moisture sensing unit 25 are described in co-pending, commonly assigned United States patent application Ser. No. 07/77,589 filed on even date herewith by Kenneth L. Schierbeek, Mark L. Larson and Kenneth Schofield entitled "CONTROL FOR A MOISTURE SENSOR", the disclosure of which is hereby incorporated by reference herein.

Referring now to FIGS. 1 and 3-16, moisture sensing unit 25 includes a carrier mounting/support block 52 preferably molded from a resinous polymeric material such as VECTRA ™ polyester resin available from Hoecht-Celanese, Chattham, N.J. to provide sufficient rigidity and support strength for the various components when mounted thereon and having a top surface 54 including surface area 54a which engages inside surface 14 of a windshield 12 as shown in FIG. 1. Carrier mounting block 52 also includes a bottom surface 56, an emitter end surface 58, and a detector end surface 60 (FIGS. 3, 4, 15 and 16). Emitter end surface 58 preferably extends at an angle of approximately 25° to a line extending normal to the window surface 14. Extending perpendicular to emitter end surface 58 are an emitter block mounting surface 62 and parallel surface 62a which lie at an angle of 25° with respect to top surface 54a (angle $\theta_1$ in FIG. 16). Likewise, detector block receiving recess 64 is defined by surfaces 65 and 67 which extend at an angle of 25° to top surface 54a and surface 66 which extends at 25° to a line normal to surface 14 (angle $\theta_3$ in FIG. 5). The axis of detector recess 64 also lies at an angle of 25° with respect to the top surface 54a (angle $\theta_2$ in FIG. 16) but opposite to the emitter mounting surface 62. Surfaces 65a and 67a, along with recess end surface 66, define an enlarged portion 68 of recess 64 for receiving a section of the detector block as described hereinafter. Detector end surface 60 includes a recessed surface 60a forming a retaining shoulder 61 (FIGS. 1, 3 and 5). Shoulder 61 engages a resilient retaining member from the mounting plate 182 when the two parts are assembled as is explained hereinafter. In addition, detector end 60 includes a slot or opening 72 extending parallel to surfaces 65, 67 and partially across the width of block 52 to provide an opening for passage of electrical wires 172 from detector mounting block 140 as explained hereinafter.

As is also shown in FIGS. 3-5, the left and right sides 72, 74 of carrier mounting block 52 extend parallel to one another and perpendicular to end surfaces 58, 60. Left side 72 includes wall 76 which closes one side of recess 64 to limit insertion of and properly position the detector mounting block 140. Flanges 78, 80 are provided in alignment with one another along surfaces 67, 65 respectively at the upper open end of recess 64 to retain and position collimators mounted on detector mounting block 140. Flanges 78, 80 continue along and extend toward one another on the inside surface of wall 76 as shown at 78a, 80a (FIGS. 3 and 5). Flanges 78a, 80a terminate at positions spaced from one another along wall 76 to provide a recess 82 for locating and positioning a radiant energy barrier wall 150 on detector mounting block 140 when positioned in the carrier block. Carrier block 52 also includes a T-shaped channel or groove 84 recessed within emitter mounting block receiving surface 62, which channel opens to the right side of the carrier block 74. Channel 84 extends approximately three-quarters of the distance across surface 62 and corresponds with a similarly T-shaped flange or tongue 130 on emitter mounting block 100 to position that block properly on carrier 52.

As is best seen in FIGS. 1, 3 and 5, carrier mounting block 52 also includes a pair of parallel, spaced retaining legs 86, 88 extending perpendicularly with respect to window engaging surface 54a. Leg 86 is adjacent emitter end surface 58 while leg 88 is flush with detector end surface 60. Legs 86, 88 include aligned slots or grooves 90, 92 adapted to slidably receive a printed circuit board 94 (FIG. 1) when the carrier mounting block is finally assembled with the remaining moisture sensing components. Alternately, printed circuit board 94 could be mounted in other ways on block 52 such as by threaded fasteners secured to the end surfaces of legs 86, 88 or by either Tinnerman spring clips or heat staking to posts extending in place of legs 86, 88.

Figure 9:
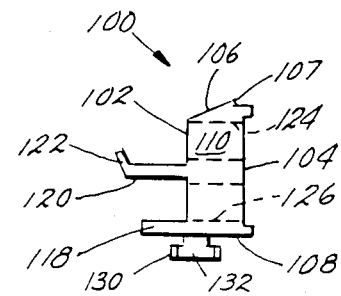
FIG. 9 is a side elevation of the emitter mounting block shown in FIGS. 6 and 7.
Figure 10:
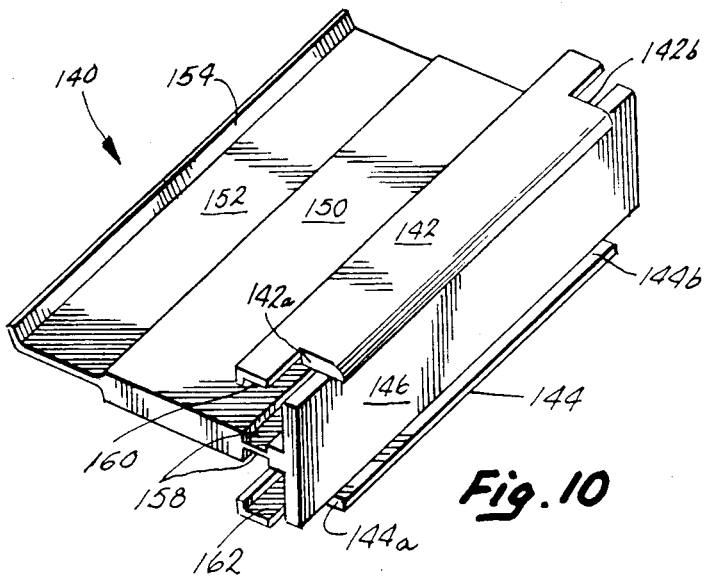
FIG. 10 is a rear perspective view of the detector mounting block prior to attachment to the carrier mounting block.
Figure 11:
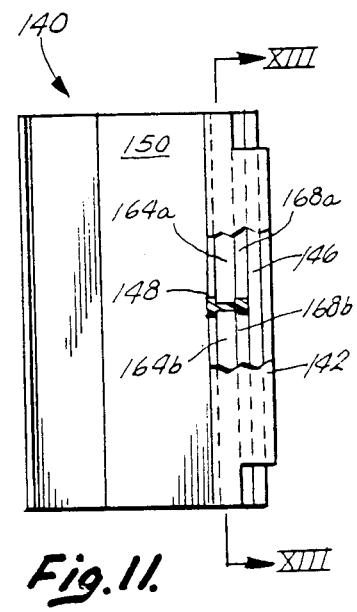
FIG. 11 is a plan view of the detector mounting block shown in FIG. 10.
Figure 13:
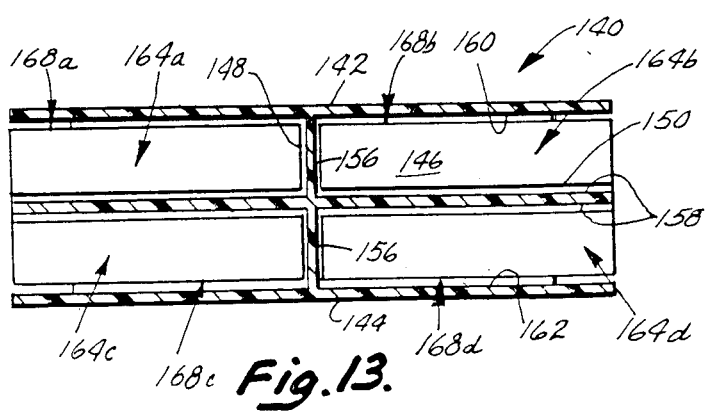
FIG. 13 is a sectional end elevation of the detector mounting block taken along plane XIII—XIII of FIG. 11.
Figure 12:
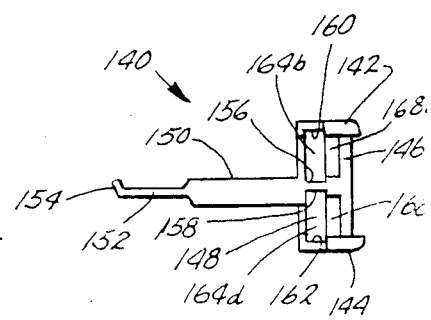
FIG. 12 is a side elevation of the detector mounting block shown in FIGS. 10 and 11.

As shown in FIGS. 6-9, an emitter block 100 is adapted to receive a plurality of infrared energy emitting diodes 39 in a stacked arrangement of two rows to provide increased infrared energy emission for sensing purposes within a defined area. Emitter block 100 includes parallel front and rear surfaces 102, 104, top and bottom surfaces 106, 108 and left and right surfaces 110, 112. Top surface 106 slants downwardly toward front surface 102 at a 25° angle such that surface 106 will be flush and co-planar with surface 54a of carrier mounting block 52 when emitter block 100 is slidably mounted on the carrier block thereby providing a window engaging surface at the emitter end of the sensing assembly. Inclined surface 107 which joins surface 106 is adapted to engage a cam surface on mounting plate 182 for positioning the sensing unit 25 in that plate. Rear surface 104 is recessed between a pair of parallel flanges 114, 116. Extending perpendicularly outwardly from spaced positions on the front surface 102 are bottom flange 118 and barrier wall 120 having an outer end 122 extending perpendicularly to top surface 106 and an angle of 115° with respect to barrier wall 118. Barrier wall 120 extends between and separates a pair of aligned rows of emitter diode receiving apertures 124, 126 which extend completely through the diode block 100 from recessed rear surface 104 to front surface 102 as shown in FIG. 9. Formed integrally with the cylindrical walls of each aperture 124, 126 are a series of three equally spaced radially inwardly projecting ribs 128 adapted to engage and tightly hold emitting diodes 39 within apertures 124, 126 upon assembly of the moisture sensing unit. The polymeric material VECTRA ™ polyester from which emitting block 100 as molded is designed to be harder than the material from which diodes 39 are formed. Thus, when diodes 39 are pressed within apertures 124, 126, diodes 39 deform and are tightly frictionally held by ribs 128.

As will be seen from FIGS. 6, 7 and 9, bottom surface 108 of emitter block 100 includes a T-shaped tongue or flange 130 which corresponds in shape and size to T-shaped slot or groove 84 in carrier mounting block surface 62. Tongue 130 extends partially across the width of block 100 from a position flush with side 112. End 132 of tongue 130 is slightly beveled or chamfered as is the open end of slot or groove 84 to facilitate insertion of the emitter block on the carrier mounting block 52 as shown in FIG. 1. When slidably inserted on the carrier block, with tongue 130 fully received in slot or groove 84, the sides 110, 112 of emitter block 100 are flush with sides 72, 74 of the carrier mounting block while bottom flange 118 lies flush with surface 62a of the carrier block. In addition, diode receiving apertures 124, 126 lie parallel to one another on axes extending at a 25° angle to the inside surface 14 and windshield engaging surfaces 106 and 54a, while barrier wall 120 lies parallel to the aperture axes and also at a 25° angle to the surfaces 106, 54a. Free end 122 of barrier wall 120 extends upwardly to a position flush or co-planar with surfaces 106, 54a such that its outer end will engage the inside surface 14 of the windshield or window when mounted as shown in FIG. 1.

As is best seen in FIG. 1, each infrared energy emitting diode 39 includes a generally cylindrical or slightly tapered bulb portion 39a, a rim or base 39b having a diameter slightly larger than the bulb portion 39a and a pair of electrical leads 39c extending outwardly from base 39b. Leads 39c are adapted to plug into and be soldered to separate portion 94a of circuit board 94 when mounted on carrier mounting block 52. A suitable infrared energy emitting diode useful in this invention is diode Model No. SE307 obtained from Nippon Electronics Corporation of Farmington Hills, Mich. However, other diodes or energy emitters could also be used although those generating energy in the infrared portion of the spectrum have been found most useful.

Referring now to FIGS. 1 and 10-14, detector block or retaining member 140 which is also preferably molded from VECTRA ™ polyester is illustrated. Detector block 140 includes top wall 142, bottom wall 144 and recessed rear wall 146. Top and bottom walls 142, 144 are inset or notched at 142a, 142b and 144a, 144b to provide access openings through which wire leads 172 from the photovoltaic sensor cells are lead into the recessed area behind wall 146 for access to wire slot 72 when detector block 140 is mounted in carrier mounting block 52. Extending from the front surface of rear wall 146 are a pair of perpendicular, interconnected walls including vertical wall 148 and barrier wall 150. Barrier wall 150 extends outwardly perpendicularly to the surface of rear wall 146 and includes a reduced thickness portion 152 at its outer end terminating in free end edge portion 154 which lies at 115° relative to wall portion 152. Walls 148, 150 include rectangular tracks or grooves 156, 158 aligned with similar rectangular tracks or grooves 160, 162 in top and bottom walls 142, 144 respectively which form filter receiving recesses 164a, 164b, 164c and 164d as shown in FIGS. 11-14. These recesses are adapted to receive infrared energy filters 166a, 166b, 166c and 166d respectiVely as shown in FIGS. 14 and 15. Immediately to the rear of the filter receiving recesses 164, are a series of four photovoltaic sensor cell receiving recesses 168a, 168b, 168c and 168d receiving photovoltaic sensor cells 170a, 170b, 170c and 170d as shown in FIGS. 1, 14 and 15. Each of the photovoltaic cells 170 is a thin, rectangular, substantially planar element having cathode and anode sides with wire leads 172 soldered to those opposite sides. A suitable photocell 170 is silicon photovoltaic cell obtained from Solar World, Inc. of Colorado Springs, Colo. However, other infrared sensors could also be used such as photodiodes or photoresistors. Cells 170 are retained against vibration and movement within recesses 168 immediately behind rectangular filter elements 166 which are tightly held in recesses 164. Barrier wall 150 extends perpendicular to the planes of filters 166 and photovoltaic cells 170 when retained in block 140 and is adapted to mount collimators 174 thereon between filters 166 and retaining flanges 78, 80 along surfaces 65, 67 as shown in FIG. 1 when mounted on carrier mounting block 52. In addition, when so mounted, barrier wall 150 extends upwardly at an angle of 25° to the inside window surface 14 such that free end edge 54 is co-planar and flush with surfaces 106, 54a for engagement with the inside window surface.

Preferably, filters 166 are thin, rectangular, substantially planar pieces of filter glass which prevent passage of radiant energy below the infrared wavelength, i.e., below 880 nanometers. A suitable glass is available from Hoya Optics, Inc. of Sturbridge, Mass. Also, collimators 174 are preferably formed honeycomb-like Hexcel (trademark) material obtained from Hexcel, Inc. of Bethel, Conn. and include a plurality of integrally formed, parallel, hexagonally-shaped tubes extending completely through the collimators from one end to the other and, in this case, parallel to the surfaces of barrier wall 150. Preferably, the openings of the tubes in collimators 174 are approximately one-sixteenth of an inch across in the preferred embodiment. Each tube is entirely coated with a black paint to absorb stray infrared energy. As used in this invention, collimators 174 limit the field of view of the photovoltaic cells 170 to that infrared energy which travels substantially parallel to barrier wall 150 and surfaces 65, 67 and to the refleCtion angle of the infrared energy from emitting diodes 39 as explained hereinafter. Thus, collimators 174 substantially eliminate extraneous and extra infrared energy not originating with emitting diodes 39.

As will now be understood from FIGS. 1, 15 and 16, emitter block 100 and detector block 140 are slidably received in carrier mounting block 52 after diodes 39 are assembled and tested in apertures 124, 126 and photovoltaic cells 170 and filter elements 166 are slidably inserted and tested in detector block 140. End 132 of tongue 130 is inserted in the open end of slot 84 and emitter block 170 is slid across the width of carrier 152 until end surfaces 110, 112 are flush with sides 72, 74 of the carrier mounting block. In such position, bottom flange 118 is flush with carrier block surface 62a as shown in FIGS. 1 and 16.

Subsequently, detector block 140 with photovoltaic cells 170 and filter elements 166 therein, is slidably inserted into recess 64 such that top and bottom walls 142, 144 are received within the detector groove 68. Detector block 140 is slid completely into recess 64 until it abuts the inside surface of wall 76 with the edge of barrier wall 150 received in recess 82. Thereafter, rectangular collimators 174 may be slid into the open areas between the surfaces of barrier wall 150 and surfaces 65, 67 and retaining flanges 78, 80. A suitable adhesive may be applied to the external surfaces of collimators 174 prior to insertion to hold them in position as described. During insertion of the detector block, the wire leads 172 from photovoltaic cells 170 are directed into notches 142, 144 and the recessed area along rear wall 146 and out through wire slot 72 in end 60 of the carrier block.

Thereafter, circuit board portion 94a having sixteen diodes 39 mounted thereon in two parallel rows spaced on centers equivalent to the spacing of apertures 124, 126 via electrical leads 39c is positioned behind the rear surface 104. All of the diodes 39 are inserted in unison into apertures 124 such that they are tightly held by crush ribs or projections 128. Alternately the diodes 39 may be separately inserted within apertures 124, 126 and thereafter connected via their electrical leads 39c to circuit board portion 94a. Next, circuit board 94 is aligned with and slid into slots 90, 92 until it is aligned and flush with sides 72, 74. Wire connectors 176 between circuit board portions 94 and 94a as well as wire leads 172 from photovoltaic cells 170, are soldered to circuit board portion 94 and the moisture sensing unit 25 is complete and ready for mounting on the inside window or windshield surface 14 as described hereinafter.

As shown in FIGS. 1 and 17-26, a protective mounting assembly 180 for supporting and detachably securing moisture sensing unit 25 against the inside surface 14 of window or windshield 12 is illustrated. As shown in FIGS. 17-20, mounting assembly 180 includes a window or windshield mounting plate 182 and a circular mounting disk or member 210. Mounting plate 182 is preferably molded from NORYL ™ EM6000 nylon polyamide resinous material available from General Electric Co. and has sufficient resiliency and flexibility to urge moisture sensing unit 25 tightly against the window surface 14 when mounted therein. Plate 182 includes a rectangular body portion 184 having a moisture sensing opening 186 at one end and a circular mounting disk receiving recess 188 positioned generally midway therealong. Recess 188 is slightly deeper than mounting disk 210. Extending along either side of opening 186 and projecting downwardly from the bottom surface of plate 194 are retaining walls 190 each including a resilient retaining member or J-shaped clip 192 centered thereon. The lower end edge of opening 186 is beveled or chamfered to form a cam surface 194 which is adapted to urge the moisture sensing unit 25 tightly into the retaining members to prevent vibration and movement when mounted on the window as explained hereinafter. In addition, locating flange 196 projects downwardly from the extreme end edge of plate 184 for engagement with lower housing 222 as shown in FIG. 18. Spaced back from the upper edge of opening 186 opposite cam surface 194 are a pair of spaced, resilient retaining projections or J-clips 198 which engage shoulder 61 on end 60 of carrier mounting block 52. Immediately adjacent and forward of projections 198 are a pair of upstanding, cylindrical fastener receiving projections 200 for engaging retaining flanges 238 from lower housing 222. Alternately, slotted, conical posts for snap fastening of the housing thereover could be used in place of projections 200. In addition, the underside of mounting disk receiving recess 88 includes an upstanding fastener receiving projection 202 for securing plate 182 and upper housing 245 to circular mounting disk 210 as explained below. The upper end of plate 182 may optionally include resilient, J-shaped retaining projections 204 for engagement with openings 206 in housing 245.

As shown in FIG. 20, circular mounting disk 210 includes a solid circular disk-shaped body portion 212 having an upstanding cylindrical mounting projection 214 centered thereon. Peripheral edge 216 of body 212 forms an annular surface which locates and guides the mounting plate 182 when recess 188 is received thereover and rotated about the mounting disk. Projection 214 is slightly smaller than recess 202 as shown in FIG. 1 and is adapted for mating reception in projection 202. Preferably, disk 210 is also molded from NORYL ™ nylon material for good bonding characteristics and high modulus of elasticity for resiliency and stiffness, and good UV stability.

Figure 21:
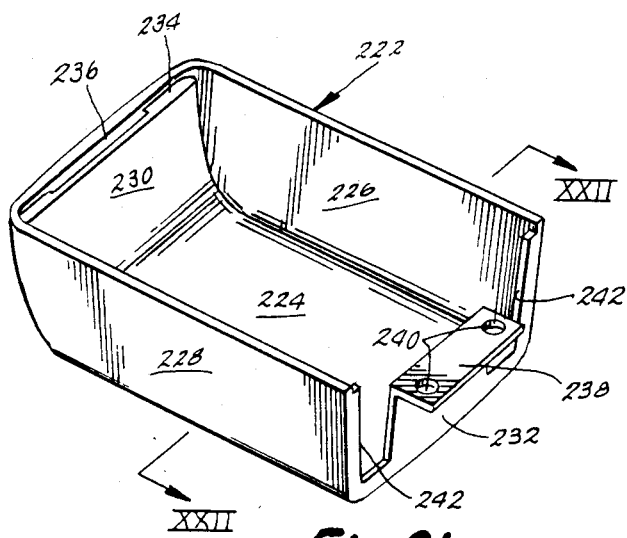
FIG. 21 is a perspective view of the lower housing for attachment to the mounting plate of the present invention.
Figure 22:
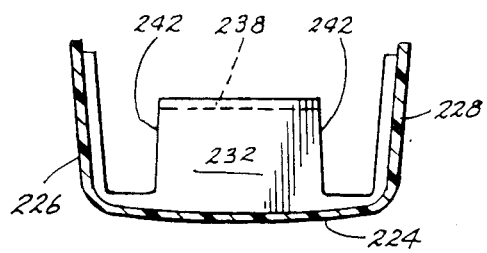
FIG. 22 is a sectional end elevation of the lower housing taken along plane XXII—XXII of FIG. 21.

As shown in FIGS. 21-24, a protective, enclosing housing assembly 220 includes a pair of mating, hollow, interconnected upper and lower sections 222, 245. Lower housing 222 includes a top wall 224, left and right sidewalls 226, 228, lower end wall 230 and upper end wall 232 (FIGS. 21 and 22). Bottom wall 230 includes a recessed ledge 234 on the inside surface thereof, which ledge also includes a rectangular recess 236 for receiving locating flange 196 on mounting plate 182. At the opposite end, wall 2 includes a securing flange 238 having fastener receiver openings 240 therein and wire openings or passageways 242 on either side of the securing flange 238.

Figure 23:
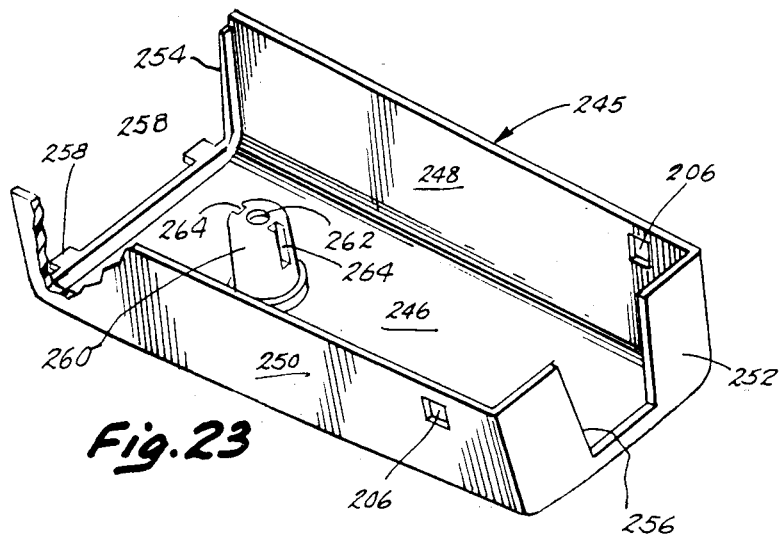
FIG. 23 is a perspective view of the upper housing of the present invention with portions broken away.

As shown in FIG. 23, upper housing 245 includes top wall 246, sidewalls 248, 250, upper end wall 252 and a U-shaped flange 254 outlining the open lower end on housing 245. Upper end wall 252 includes a wire passageway or opening 256 recessed therein, while flange 254 at the lower end opening includes spaced, parallel connecting tabs 258 sized to correspond to and be received within the lower portions of wire passageways 242 in lower housing 222. In addition, a cylindrical fastening projection 260 is molded to project inwardly from the inside surface of top wall 246 in upper housing 245 and includes a fastener receiving aperture 262 and screw cover retaining slots 264 molded therein. As mentioned above, the upper end of upper housing 245 may also include apertures 206 for receiving retaining members 204. Preferably, lower and upper housing sections 222, 245 are preferably molded from NORYL ™ nylon.

Figure 25:
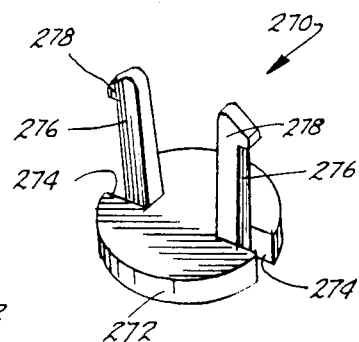
FIG. 25 is a perspective view of the fastener cover for assembly with the upper housing.
Figure 24:
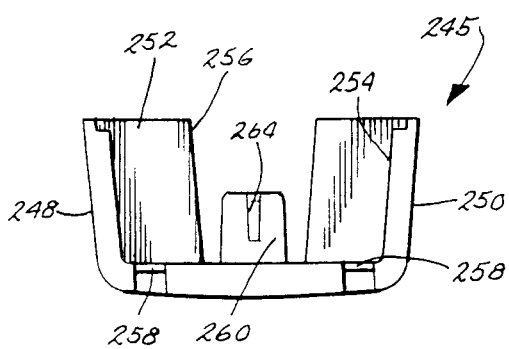
FIG. 24 is an end elevation of the upper housing shown in FIG. 23.
Figure 26:
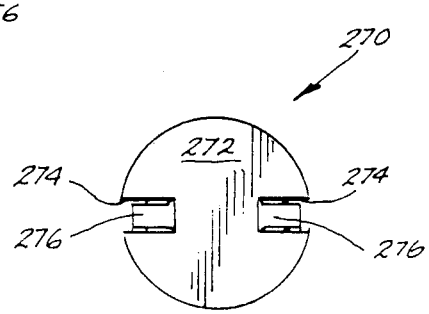
FIG. 26 is a plan view of the fastener cover shown in FIG. 25.

As shown in FIGS. 25 and 26, a screw cover or plug 270 is illustrated. Cover 270 includes a disk-like top 272 having diametrically opposed slots 274 from which extend resilient retaining members or posts 276 having J-shaped configurations and shoulders 278 for retaining the cover in place. Like housings 222, 245, cover 270 is preferably molded from NORYL ™ nylon.

As will now be understood from FIG. 1, assembly of the moisture sensing unit 25 to the mounting assembly 180 and then to the inside window surface 14 will now be understood. The previously assembled moisture sensing unit 25 including circuit boards 94 and 94a thereon is slidably inserted toward retaining projections 198 in the opening between walls 190 on plate 182 from the direction of cam surface 194. After shoulder 61 is engaged with retaining projections 198, carrier mounting block 52 is pressed downwardly until retaining projections 192 snap over the bottom surface 56 of the carrier block and beveled surface 107 on emitting block 100 engages cam surface 194 on mounting plate 182. Such engagement urges the entire moisture sensing unit 25 toward retaining members 198 and 192 such that it is tightly held to retaining plate 182.

After assembly of the moisture sensing unit 25 to plate 182, lower housing 222 is assembled over the lower end of the plate and moisture sensing unit by locating flange 96 on plate 182 in recess 236 and swinging the lower housing section over the moisture sensing unit until flange 38 engages the top surfaces of projections 200 and apertures 240 are aligned with the openings in those mounting projections. Threaded fasteners or screws 280 are then inserted through apertures 240 and into projections 200 to secure the lower housing in place. Electrical wiring 22 leading from circuit board section 94 is passed through openings 242.

Subsequently, circular mounting disk 210 is secured to the inside surface 14 of window or windshield 12 toward the upper edge of the windshield and the upper edge of the windshield wiper clearing or sweep area by means of double-faced tape or another suitable adhesive layer 218. The orientation of the circular disk 210 is not critical since mounting plate 182 including moisture sensor unit 25 and lower housing 222 secured thereon may be rotated about the disk 210 to orient the moisture sensor properly during installation. Once the circular mounting disk 210 is in place, plate 182 with moisture sensor unit 25 and lower housing 222 mounted thereon is installed with recess 188 and projection 202 receiving disk body 212 and projection 214 as shown in FIG. 1. Plate 182 may then be rotated around the circular disk to position the moisture sensing unit 25 in the desired position within the windshield wiper sweep area.

Next, upper housing 245 is assembled to the upper portion of plate 182 and interconnected with lower housing 222 by inserting projecting tabs 258 into openings 242. Securing projection 260 is then brought into contact with the top surface of projection 202. Simultaneously, resilient fasteners 204 are snapped into place in openings 206 in upper housing sides 248, 250 to retain the housing on plate 182. Threaded fastener or screw 282 is then inserted through aperture 262 in fastener projection 260 and tightened through projection 202 and into projection 214 on the mounting disk to secure the assembly on the windshield.

After the combined mounting plate, moisture sensing unit and housing assembly is secured to the windshield with screw 282, screw cover 270 is snapped into place in the opening to fastening projection 260 from the exposed side of top 246 of upper housing 245 as shown in FIG. 1. Plug 270 thus covers and conceals the fastening screw from the interior of the vehicle. Removal of the cover 270 is accomplished by inserting a thin projection into slots 274 and bending members 276 inwardly such that ends 278 are no longer in contact with slots 264 and the cover can be removed.

As will be understood from FIG. 1, the depth of recess 188 in plate 182 is sufficient to receive the full thickness of mounting disk 210 when fastener 282 is properly secured. This forces the underside of plate 182 tightly into contact with the inside surface 14 of windshield 12. Because of the natural curvature of windshields and/or windows in modern vehicles, the lower end of plate 182 including flange 196, moisture sensor 25 and housing section 222, are forced somewhat inwardly toward the interior of the vehicle with respect to the position of mounting disk 210 which is spaced several inches thereabove on the windshield. Such slight inward positioning causes a flexing of plate 182. The natural resiliency of the plate, as stiffened and reinforced by walls 190, urges the plate toward the inside windshield surface causing moisture sensing unit surfaces 106 and 54a to be tightly pressed against the inside surface of the windshield. Also, free ends 122, 154 of barrier walls 120, 150 are urged tightly into contact with the inside surface 14 of the windshield to block reflected radiant energy rays other than those properly refracted through the windshield and reflected from the exterior surface 16 of the windshield or window and any moisture or other matter thereon as shown in FIG. 1. Depending on the curvature of the windshield, the length of stiffening walls 190 may be adjusted during manufacture of the plate 182 to provide more or less resiliency and thus more or less biasing force for urging the moisture sensing unit against the inside windshield surface. Similarly, the thickness of the plate 182 may be changed to help increase the stiffness and resiliency.

Wiring 22 from moisture sensing unit 25 is passed through upper housing section 245 and out opening 256 and into the header portion of the vehicle for connection to the electrical system of the vehicle. Thus, the combined housing sections enclose, cover and shield any electrical wiring extending from the moisture sensing unit 25.

In operation, pulsed infrared energy emitted by diodes 39 passes outwardly through the openings between window engaging surfaces 106, 54a of moisture sensing unit 25 to the air/glass interface at the inside surface 14 of windshield 12. There, due to the index of refraction of the windshield glass, it is refracted outwardly to the outer air/glass surface at the exterior surface 16 of the windshield. In the absence of any moisture or dust particles on the outside of the windshield, such as after wiping, a substantial portion of the infrared energy is reflected by the air/outside windshield surface interface back into collimators 174, filters 166 and photovoltaic cells 170. However, when moisture such as water drops M are present on the outside windshield surface, the infrared energy is scattered at the air/outside windshield surface interface such that lesser amount of infrared energy is reflected back into photovoltaic cells 170. Such decreased amount of reflected energy is sensed by cells 170 and is indicated to control circuit 34 (FIG. 2) to initiate wiping action. Alternatively, should dust, dirt or salt residue particles be present on the outside of the windshield, a greater amount of infrared energy would be reflected to photovoltaic cells 17 which would be indicated to control circuit 34 as a higher amount of energy. In the preferred embodiment, such signaling is ignored but could be used in other systems to activate windshield washing or spraying action in combination with wiping action to clean the windshield and remove the other matter.

It will also be understood that the stacked arrangement of diodes 39 and collimators 174, filters 166 and sensing cells 170 enables sensing over a substantially wider area of the outside windshield surface than with a single row of emitters and detectors as in previous devices. Thus, as shown in FIG. 1, the row of diodes 39 closest to the inside windshield surface 14 emits infrared energy along energy path A which is refracted and reflected to the row of sensing cells 170 farthest from the windshield. During such operation, the remaining row of diodes 39 and the sensing cells 170 closest to the windshield are deenergized and nonoperative. In combination with the energy barrier walls 120, 150, such alternating operation prevents the false triggering of the device by extraneous or reflected energy. Following pulsing of the row of diodes 39 closest to the window, the row farthest from the windshield is subsequently pulsed emitting energy along path B to the collimator, filter and row of sensing cells 170 closest to the windshield. Simultaneously, upper diode row 39 and lower sensing cells 170 along path A are deenergized and inoperative. As shown in FIG. 1, paths A and B intersect one another between barrier walls 120, 150 and interior of window surface 14 and the plane of surfaces 54a, 106. Accordingly, the present arrangement allows alternate rows of diodes and sensing cells to operate successively to avoid interference with operation of the other rows and to sense an increased area of the windshield surface to provide more accurate sensitivity to moisture all while reducing and maintaining the overall sensor size to a compact form. Extraneous reflected rays (shown by the dotted lines in FIG. (1) are blocked by the barrier walls and eliminated from sensing by the operation of the electrical circuit 26.

While several forms of the invention have been shown and described, other forms will now be apparent to those skilled in the art. Therefore, it will be understood that the embodiments shown in the drawings and described above are merely for illustrative purposes, and are not intended to limit the scope of the invention which is defined by the claims which follow.

The embodiments of the invention in which an exclusive property or privilege is claimed are defined as follows:

1. A moisture sensing assembly for mounting on one surface of a window to detect and indicate moisture or other matter accumulated on the opposite surface of the window, said assembly comprising:
first and second emitter means for emitting radiant energy toward the window;
first and second detector means for detecting and receiving radiant energy from said first and second emitter means respectively after reflection and refraction by the window and any accumulated moisture or other matter on the opposite surface of the window;
radiant energy barrier means for preventing reflection of radiant energy from said first emitter means and the one surface of the window to said first and second detector means, and for preventing reflection of radiant energy from said second emitter means and the one surface of the window to said second detector means; and
support means for supporting said first and second emitter means in spaced angular relationship to said first and second detector means and said radiant energy barrier means on the one window surface;
said support means including a window engaging surface for engaging the one window surface; said support means including means for spacing one of said emitter means farther from said support surface than the other of said emitter means and for spacing one of said detector means farther from said support surface than the other of said detector means;
said radiant energy barrier means including a first radiant energy barrier extending between said first and second emitter means to a position aligned with said support surface and a second radiant energy barrier extending between said first and second detector means to a position aligned with said support surface; said first and second radiant energy barriers adapted to engage the one window surface when said assembly is mounted thereon with said window engaging surface engaging the one window surface.

2. The assembly of claim 1 including mounting means for releasably mounting said support means on the one surface of the window such that said window engaging surface on said support means will engage the window; and housing means for covering said emitter means, detector means and barrier means when mounted on the window with said mounting means.

3. The assembly of claim 1 including mounting means for releasably mounting said support means on the one surface of the window such that said window engaging surface on said support means will engage the window, said mounting means including means for urging said support means tightly against portions of said mounting means.

4. A moisture sensing assembly for mounting on one surface of a window to detect and indicate moisture or other matter accumulated on the opposite surface of the window, said assembly comprising:
first and second emitter means for emitting radiant energy toward the window;
first and second detector means for detecting and receiving radiant energy from said first and second emitter means respectively after reflection and refraction by the window and any accumulated moisture or other matter on the opposite surface of the window;
radiant energy barrier means for preventing reflection of radiant energy from said first emitter means and the one surface of the window to said first and second detector means, and for preventing reflection of radiant energy from said second emitter means and the one surface of the window to said second detector means; and
support means for supporting said first and second emitter means in spaced angular relationship to said first and second detector means and said radiant energy barrier means on the one window surface;
said radiant energy barrier means including first and second radiant energy barriers spaced from one another, said first radiant energy barrier extending between and separating said first and second emitter means and being adapted to engage the one window surface.

5. The moisture sensing assembly of claim 4 wherein said second radiant energy barrier extends between and separates said first and second detector means and is adapted to engage the one window surface.

6. The assembly of claim 5 wherein said support means includes a mounting block having a window engaging surface, a first pair of apertures for mounting said first and second emitting means, one of said apertures in said first pair being closer to said window engaging surface than the other of said apertures, said first radiant energy barrier means including a first wall extending between said first pair of apertures and outwardly from said apertures to a position substantially flush with said window engaging surface.

7. The assembly of claim 6 wherein said first pair of apertures and said first wall are formed on an emitter block; said assembly including means for removably mounting said emitter block on said mounting block such that said first pair of apertures and first wall lie at an angle to said window engaging surface.

8. The assembly of claim 6 wherein said first and second emitting means each include an infrared emitting source.

9. The assembly of claim 6 wherein said mounting block includes a second pair of apertures for mounting said first and second detector means, one of said apertures in said second pair being closer to said window engaging surface than the other of said apertures, said second radiant energy barrier means including a second wall extending between said second pair of apertures and outwardly from said openings to a position substantially flush with said window engaging surface.

10. The assembly of claim 9 wherein said second pair of apertures and said second wall are formed on a detector retaining member; said assembly including means for removably mounting said detector retaining member on said mounting block such that said pair of openings and second wall lie at an angle to said window engaging surface.

11. The assembly of claim 10 wherein said first and second detector means each include an infrared energy sensor.

12. The assembly of claim 11 wherein said detector means each also include a collimator and energy filter mounted between said emitting means and said sensor.

13. The assembly of claim 9 wherein said mounting block includes at least one additional pair of apertures for mounting additional detector means in alignment with said first and second detector means whereby first and second rows of detecting means are formed; said second radiant energy barrier means extending between said first and second rows of detecting means.

14. The assembly of claim 6 wherein said mounting block includes at least one additional pair of apertures for mounting additional emitting means in alignment with said first and second emitting means whereby first and second rows of emitting means are formed; said first radiant energy barrier means extending between said first and second rows of emitting means.

15. A moisture sensing assembly for mounting on one surface of a window to detect and indicate moisture or other matter accumulated on the opposite surface of the window, said assembly comprising:

first and second emitter means for emitting radiant energy toward the window;

first and second detector means for detecting and receiving radiant energy from said first and second emitter means respectively after reflection and refraction by the window and any accumulated moisture or other matter on the opposite surface of the window;

radiant energy barrier means for preventing reflection of radiant energy from said first emitter means and the one surface of the window to said first and second detector means, and for preventing reflection of radiant energy from said second emitter means and the one surface of the window to said second detector means; and support means for supporting said first and second emitter means in spaced angular relationship to said first and second detector means and said radiant energy barrier means on the one window surface; said support means including a rigid mounting block having one surface adapted to engage the one surface of the window, a first pair of apertures therein for receiving said first and second emitter means, and a second pair of apertures therein for receiving said first and second detector means.

16. The assembly of claim 15 wherein each of said pairs of apertures is positioned in a stacked arrangement with one aperture in each pair being closer to said window engaging surface than the other aperture in each pair.

17. The assembly of claim 16 wherein said first and second energy barrier means extend between said first and second pairs of apertures respectively and outwardly of said apertures to respective positions substantially flush with said window engaging surface.

18. The assembly of claim 15 wherein said support means includes means for mounting a circuit board thereon.

19. A moisture sensing assembly for mounting on one surface of a window to detect and indicate moisture or other matter accumulated on the opposite surface of the window, said assembly comprising:

first and second emitter means for emitting radiant energy toward the window;

first and second detector means for detecting and receiving radiant energy from said first and second emitter means respectively after reflection and refraction by the window and any accumulated moisture or other matter on the opposite surface of the window;

support means for supporting said first and second emitter means in spaced angular relationship to said first and second detector means on the one window surface; said support means including a window engaging surface; said first emitter means and said second detector means being closer to said window engaging surface than said second emitter means and said first detector means.

20. The assembly of claim 19 wherein said support means includes a mounting block having a first pair of apertures for mounting said first and second emitter means and a second pair of apertures for mounting said first and second detector means, one of said apertures in each of said first and second pairs being closer to said window engaging surface than the other of said apertures.

21. The assembly of claim 20 including radiant energy barrier means for preventing reflection of radiant energy from said first emitter means and the one surface of the window to said first and second detector means, and for preventing reflection of radiant energy from said second emitter means and the one surface of the window to said second detector means.

22. The assembly of claim 21 wherein said radiant energy barrier means include a first wall extending between said first pair of apertures and outwardly from said apertures to a position substantially flush with said window engaging surface and a second wall extending between said second pair of apertures and outwardly from said openings to a position substantially flush with said window engaging surface.

23. The assembly of claim 22 wherein said first pair of apertures and said first wall are formed on an emitter block; said assembly including means for removably mounting said emitter block on said mounting block such that said first pair of apertures and first wall lie at an angle to said window engaging surface; said second pair of apertures and said second wall are formed on a detector retaining member; said assembly including means for removably mounting said detector retaining member on said mounting block such that said pair of openings and second wall lie at an angle to said window engaging surface.

24. The assembly of claim 20 wherein said mounting block includes at least one additional pair of apertures for mounting additional emitting means in alignment with said first and second emitting means whereby first and second rows of emitting means are formed; said mounting block includes an additional pair of apertures for mounting additional detector means in alignment with said first and second detector means whereby first and second rows of detecting means are formed.

25. A moisture sensing assembly for mounting on one surface of a window to detect and indicate moisture or other matter accumulated on the opposite surface of the window, said assembly comprising:

first and second emitter means for emitting radiant energy toward the window;

first and second detector means for detecting and receiving radiant energy from said first and second emitter means respectively after reflection and refraction by the window and any accumulated moisture or other matter on the opposite surface of the window;

support means for supporting said first and second emitter means in spaced angular relationship to said first and second detector means on the one window surface, said emitter means being positioned such that the path followed by radiant energy emitted by said first emitter means intersects the path followed by radiant energy emitted by said second emitter means at a position prior to reception by said first and second detector means; and radiant energy barrier means for engaging the one window surface to prevent reflection of radiant energy from said first emitter means and the one surface of the window to said first and second detector means, and to prevent reflection of radiant energy from said second emitter means and the one surface of the window to said second detector means.

26. A moisture sensing assembly for mounting on one surface of a window to detect and indicate moisture or other matter accumulated on the opposite surface of the window, said assembly comprising:

first and second emitter means for emitting radiant energy toward the window;

first and second detector means for detecting and receiving radiant energy from said first and second emitter means respectively after reflection and refraction by the window and any accumulated moisture or other matter on the opposite surface of the window;

support means for supporting said first and second emitter means in spaced angular relationship to said first and second detector means on the one window surface, said emitter means being positioned such that the path followed by radiant energy emitted by said first emitter means intersects the path followed by radiant energy emitted by said second emitter means at a position prior to reception by said first and second detector means, said support means including a mounting block having a first pair of apertures for mounting said first and second emitter means and a second pair of apertures for mounting said first and second detector means, one of said apertures in each of said first and second pairs being closer to said window engaging surface than the other of said apertures.

27. The assembly of claim 26 including radiant energy barrier means for preventing reflection of radiant energy from said first emitter means and the one surface of the window to said first and second detector means, and for preventing reflection of radiant energy from said second emitter means and the one surface of the window to said second detector means.

28. The assembly of claim 27 wherein said radiant energy barrier means include a first wall extending between said first pair of apertures and outwardly from said apertures to a position substantially flush with said window engaging surface and a second wall extending between said second pair of apertures and outwardly from said openings to a position substantially flush with said window engaging surface.

29. The assembly of claim 28 wherein said position at which said radiant energy paths intersect is intermediate said first and second barrier walls and spaced from said window engaging surface.

30. A mounting block for supporting moisture sensing apparatus on one surface of a window for detecting and indicating moisture or other matter accumulated on the opposite surface of the window, said block comprising:

a rigid carrier body;

emitter mounting means for mounting emitter means for emitting radiant energy toward the window;

detector mounting means for mounting detector means for detecting and receiving radiant energy from said emitter means after reflection and refraction by the window and any accumulated moisture or other matter on the opposite surface of the window;

first means for removably attaching said emitter mounting means on one portion of said carrier body; and second means for removably attaching said detector mounting means on a second portion of said carrier body.

31. The mounting block of claim 30 wherein said first and second means include means for slidably receiving said emitter mounting means and detector mounting means, respectively.

32. The mounting block of claim 31 wherein said means for slidably receiving said emitter mounting means include a tongue on one of said body and said emitter mounting means and a mating groove on the other of said body and said emitter mounting means.

33. The mounting block of claim 32 wherein said tongue and groove extend only partially across said body and emitter mounting means said groove including a closed end to limit insertion of and locate said tongue and emitter mounting means.

34. The mounting block of claim 31 wherein said means for slidably receiving said detector mounting means include a configured recess in said rigid carrier body.

35. The mounting block of claim 34 including a wall closing one end of said configured recess to limit insertion of and locate said detector mounting means.

36. The mounting block of claim 30 including circuit board mounting means for mounting a circuit board on said mounting block.

37. The mounting block of claim 36 wherein said circuit board mounting means include a pair of spaced legs extending outwardly from said body, said legs including means for removably mounting the circuit board thereon.

38. The mounting block of claim 30 wherein said emitter mounting means and detector mounting means are spaced from one another and are supported on said body at an angle to one another.

39. The mounting block of claim 38 wherein said body includes a window engaging surface; said emitter mounting means and said detector mounting means each being mounted at an equivalent angle to said window engaging surface.

40. The mounting block of claim 39 wherein said emitter mounting means includes an emitter block having at least one pair of diode receiving apertures arranged with their axes parallel to one another and one aperture closer to said window engaging surface than the other, and a radiant energy barrier wall extending between said apertures to a position substantially flush with said window engaging surface.

41. The mounting block of claim 40 wherein each of said diode receiving apertures includes at least one projection therein for frictionally engaging a diode when inserted in said aperture.

42. The mounting block of claim 39 wherein said detector mounting means includes a detector block having at least one pair of photosensor receiving apertures arranged with their axes parallel to one another and one aperture closer to said window engaging surface than the other, and a radiant energy barrier wall extending between said apertures to a position substantially flush with said window engaging surface.

43. A moisture sensing assembly especially adapted for controlling vehicle accessories such as windshield wipers comprising:
    a moisture sensing unit for engaging one surface of a window to detect and indicate moisture or other particles on the opposite window surface;
    a mounting member for attachment to the one surface of the window;
    mounting means for engaging said mounting member and releasably mounting said moisture sensing unit on the one window surface, said mounting member and said mounting means including positioning means having a circular shape including means for positioning said moisture sensing unit and said mounting means as desired around said mounting member; and
    releasable fastening means for holding said mounting member and mounting means together until released.

44. The assembly of claim 43 wherein said mounting means includes a resilient plate having an opening and a plurality of resilient retaining members for holding said moisture sensing unit adjacent and in registry with said opening, said plate being sufficiently resilient to urge said sensing unit toward the window when flexed from its initial condition in a direction away from the window.

45. The assembly of claim 44 wherein said plate includes camming means for urging said moisture sensing unit tightly against said resilient retaining members.

46. The assembly of claim 44 wherein said positioning means include a circular recess in said plate for receiving said mounting member, said recess allowing rotation of said plate and moisture sensing unit about said mounting member.

47. The assembly of claim 46 wherein said mounting member is a circular disk adapted to be adhered to the one window surface, said releasable fastening means include an upstanding projection on said disk for fastening said plate to said disk and a recess for receiving said projection.

48. The assembly of claim 43 including housing means for covering said moisture sensing means and releasable securing means for securing said housing means on said mounting means.

49. The assembly of claim 48 including second housing means for covering said mounting member and second releasable securing means for securing said second housing means on said mounting means.

50. The assembly of claim 49 including means for connecting said second housing means to said housing means; said releasable fastening means including said second releasable securing means.

51. The assembly of claim 50 wherein said releasable fastening means includes a threaded fastener engaging said second housing, said mounting means, and said mounting member.

52. The assembly of claim 49 wherein said housing and second housing means include means for enclosing, covering and shielding any electrical wiring extending from said moisture sensing unit.

53. The assembly of claim 48 including a locating flange extending outwardly from said mounting means for engaging and positioning said housing means thereon, said housing means including a recess for receiving said locating flange therein.

* * * * *

UNITED STATES PATENT AND TRADEMARK OFFICE
CERTIFICATE OF CORRECTION

PATENT NO. : 4,973,844

DATED : November 27, 1990

INVENTOR(S) : Desmond J. O'Farrell and Kenneth L. Schierbeek

It is certified that error appears in the above-identified patent and that said Letters Patent is hereby corrected as shown below:

Title Page:

In the Abstract, line 4:

"are a being" should be --area being--

Column 1, line 44:

"4,871,927" should be --4,871,917--

Column 6, line 68:

"07,77,589" should be --07/377,589--

Column 9, line 43:

"respectiVely" should be --respectively--

Column 10, lines 19 and 20:

"refleCtion" should be --reflection--

Column 12, line 2:

"wall 2" should be --wall 232--

Column 12, line 50:

"flange 96" should be --flange 196--

UNITED STATES PATENT AND TRADEMARK OFFICE
CERTIFICATE OF CORRECTION

PATENT NO. : 4,973,844

DATED : November 27, 1990

INVENTOR(S) : Desmond J. O'Farrell and Kenneth L. Schierbeek

It is certified that error appears in the above-identified patent and that said Letters Patent is hereby corrected as shown below:

Column 12, line 52:

"flange 38" should be --flange 238--

Column 14, line 16:

After "that" insert --a--

Column 14, line 23:

"cells 17" should be --cells 170--

Signed and Sealed this

Fourteenth Day of July, 1992

Attest:

DOUGLAS B. COMER

Attesting Officer

Acting Commissioner of Patents and Trademarks